US009233250B2

United States Patent
Shelchuk et al.

(10) Patent No.: US 9,233,250 B2
(45) Date of Patent: Jan. 12, 2016

(54) SYSTEMS AND METHODS TO SYNCHRONIZE COMMANDS SENT TO A MULTI-ELECTRODE LEAD (MEL) WITH A PORTION OF A CARDIAC PACING CYCLE

(75) Inventors: Anne Shelchuk, Cupertino, CA (US); Yongjian Wu, Saratoga, CA (US); Chris Pontiga, Sunnyvale, CA (US); April Pixley, Los Altos, CA (US); Pajhand Iranitalab, San Ramon, CA (US); Elisabeth M. Clem, Redwood City, CA (US); Shohan Hossain, Maple Grove, MN (US); Jianchun Yi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 678 days.

(21) Appl. No.: 12/648,599

(22) Filed: Dec. 29, 2009

(65) Prior Publication Data

US 2011/0046690 A1 Feb. 24, 2011

Related U.S. Application Data

(60) Provisional application No. 61/234,945, filed on Aug. 18, 2009.

(51) Int. Cl.
*A61N 1/00* (2006.01)
*A61N 1/368* (2006.01)
*A61N 1/37* (2006.01)
*A61N 1/39* (2006.01)

(52) U.S. Cl.
CPC .............. *A61N 1/368* (2013.01); *A61N 1/3686* (2013.01); *A61N 1/3684* (2013.01); *A61N 1/3704* (2013.01); *A61N 1/3912* (2013.01)

(58) Field of Classification Search
CPC ..... A61N 1/368; A61N 1/3684; A61N 1/3686; A61N 1/3704; A61N 1/3912
USPC ......................................... 607/4–38, 119–132
See application file for complete search history.

(56) References Cited

U.S. PATENT DOCUMENTS 4,991,583 A * 2/1991 Silvian ............................ 607/13
5,871,510 A * 2/1999 Kroll et al. ...................... 607/14

(Continued)

FOREIGN PATENT DOCUMENTS

| EP | 1682219 | 7/2006 |
|---|---|---|
| WO | 2005032655 | 4/2005 |
| WO | 2005032656 | 4/2005 |

*Primary Examiner* — Niketa Patel
*Assistant Examiner* — Lindsey G Hankins
(74) *Attorney, Agent, or Firm* — Theresa A. Raymer

(57) ABSTRACT

Embodiments of the present invention concern the timing of sending one or more commands to control circuitry of a multi-electrode lead (MEL). In one embodiment, the one or more commands are sent to control circuitry within the MEL during a predetermined portion of a cardiac pacing cycle to avoid potential problems of prior systems that were not synchronized with the cardiac pacing cycle. In one embodiment, the one or more commands are sent when cardiac tissue is refractory from a cardiac pacing pulse, to prevent the command(s) from potentially undesirably stimulating cardiac tissue. The command sending can occur such that the one or more commands are sent between instances when sensing circuitry of the implantable cardiac stimulation device is being used to obtain one or more signals indicative of cardiac electrical activity, to prevent interference between the one or more commands with the signals indicative of cardiac electrical activity that are sensed.

25 Claims, 7 Drawing Sheets

(56) References Cited

U.S. PATENT DOCUMENTS

| | | | |
|---|---|---|---|
| 6,473,653 B1 * | 10/2002 | Schallhorn et al. | 607/116 |
| 7,200,437 B1 | 4/2007 | Nabutovsky | |
| 7,218,966 B2 | 5/2007 | Haefner | |
| 7,236,819 B2 | 6/2007 | Brockway | |
| 2003/0144704 A1 * | 7/2003 | Terry et al. | 607/27 |
| 2003/0149456 A1 * | 8/2003 | Rottenberg et al. | 607/37 |
| 2004/0230129 A1 | 11/2004 | Haefner | |
| 2005/0075683 A1 | 4/2005 | Miesel | |
| 2005/0119708 A1 | 6/2005 | Haefner | |
| 2006/0058588 A1 | 3/2006 | Zdeblick | |
| 2007/0293896 A1 | 12/2007 | Haefner | |
| 2009/0018599 A1 | 1/2009 | Hastings | |
| 2009/0062879 A1 | 3/2009 | Li | |
| 2009/0062880 A1 * | 3/2009 | Li et al. | 607/32 |
| 2009/0270943 A1 * | 10/2009 | Maschino | 607/45 |

* cited by examiner

SYSTEMS AND METHODS TO SYNCHRONIZE COMMANDS SENT TO A MULTI-ELECTRODE LEAD (MEL) WITH A PORTION OF A CARDIAC PACING CYCLE

PRIORITY CLAIM

This application claims priority under 35 U.S.C. §119(e) to U.S. Provisional Patent Application No. 61/234,945, filed Aug. 8, 2009, which is incorporated herein by reference.

FIELD OF THE INVENTION

Embodiments of the present invention relate to implantable cardiac systems and leads for use therewith. More specifically, embodiments of the present invention relate to systems and methods using a Multi-Electrode Lead (MEL).

BACKGROUND OF THE INVENTION

In the normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A-V) node and a ventricular conduction system causing a depolarization known as an R-wave and the resulting ventricular chamber contractions.

Disruption of this natural pacing and conduction system as a result of aging or disease can be successfully treated by artificial cardiac pacing using implantable cardiac stimulation devices, including pacemakers and implantable defibrillators, which deliver rhythmic electrical pulses or anti-arrhythmia therapies to the heart at a desired energy and rate. A cardiac stimulation device is electrically coupled to the heart by one or more leads possessing one or more electrodes in contact with the heart muscle tissue (myocardium). One or more heart chambers may be electrically stimulated depending on the location and severity of the conduction disorder.

A stimulation pulse delivered to the myocardium must be of sufficient energy to depolarize the tissue, thereby causing a contraction, a condition commonly known as "capture". In early pacemakers, a fixed, high-energy pacing pulse was delivered to ensure capture. While this approach is straightforward, it quickly depletes battery energy and can result in patient discomfort due to extraneous extracardiac stimulation, e.g., of surrounding skeletal muscle tissue, the patient's phrenic nerve or the patient's diaphragm.

The "capture threshold" is defined as the lowest stimulation pulse energy at which capture occurs. By stimulating the heart chambers at or just above this threshold, comfortable and effective cardiac stimulation can be provided without unnecessary depletion of battery energy. The capture threshold, however, is extremely variable from patient-to-patient due to variations in electrode systems used, electrode positioning, physiological and anatomical variations of the heart itself, and so on. Furthermore, a capture threshold may vary over time within a patient as, for example, fibrotic encapsulation of an electrode can occur after implantation of the electrode.

Implantable lead(s), attached to an implantable pulse generator (IPG), such as a pacemaker and/or implantable cardioverter defibrillator (ICD), is/are used to deliver such stimulation pulses to the myocardium. Some such leads are Multi-Electrode Leads (MELs), meaning they include multiple electrodes for use in pacing and/or sensing. MELs allow for more flexibility in pacing and sensing, as compared to single electrode leads. Generally, the more electrodes on a lead, the more flexibility provided. For example, one lead design includes four electrode arrays (also referred to as groups or bands) with four electrodes each, thus resulting in a single lead with sixteen electrodes. An example of a lead that can include sixteen (and even more) electrodes is disclosed in U.S. Patent Publication No. 2006/0058588 (U.S. patent application Ser. No. 11/219,305), entitled "Methods and Apparatus for Tissue Activation and Monitoring" (Zdeblick), published Mar. 16, 2006 (filed Sep. 1, 2005), which is incorporated herein by reference.

With some MELs, such as the MEL described in Zdeblick, one or more commands can be sent to control circuitry of the MEL to configure the electrodes. A configuration of the MEL can have one or more of the electrodes connected as an anode, one or more of the electrodes connected as a cathode, and other of the electrodes disconnected. After the MEL is configured, the connected electrodes can be used for pacing and/or sensing. The same multi-conductor bus in the MEL can be used for configuring the electrodes, for pacing and for sensing.

SUMMARY OF THE INVENTION

Embodiments of the present invention concern the timing of the sending of one or more commands to control circuitry within a MEL.

In prior systems, the MEL commands were sent to the control circuitry in the lead without being synchronized with the cardiac pacing cycle. This can cause problems since the commands can accidently interfere with the pacing and/or sensing.

In one embodiment of the present invention, the one or more commands are sent to control circuitry within the MEL during a predetermined portion of a cardiac pacing cycle. This avoids the problems of the prior systems that were not synchronized with the cardiac pacing cycle, since, in the present invention, the one or more commands can be sent when they would not interfere with the pacing and/or sensing.

In one embodiment, the one or more commands are sent to the control circuitry of the MEL when cardiac tissue is refractory from a cardiac pacing pulse. This prevents the commands from undesirably stimulating cardiac tissue. In prior system, commands sent when the cardiac tissue is not refractory can potentially inadvertently cause capture.

The sending of the commands can occur such that the one or more commands are sent between instances when sensing circuitry of the implantable cardiac stimulation device is being used to obtain one or more signals indicative of cardiac electrical activity. Sending the one or more commands at this time prevents the commands from interfering with the sensed signals.

The sending of the commands can be done during an initial charge balancing portion of the cardiac pacing pulse. This can allow any charge from the commands to be removed by the charge balancing of the initial charge balancing portion. The initial charge balancing period can be a "fast discharge" portion in which the charge balancing is done at a relatively fast rate as compared to a later "slow discharge" period.

The sending of the one or more commands can interrupt charge balancing during the initial charge balancing portion. In one example, a controller can disconnect the charge balancing to send the one or more commands.

The sending step can begin a predetermined delay after a specified feature of a primary pace pulse portion. The predetermined delay can be such that the commands are sent during the initial charge balancing portion.

This summary is not intended to be a complete description of, or limit the scope of, the invention. Alternative and additional features, aspects and objects of the invention can be obtained from a review of the specification, Figures and the claims.

DETAILED DESCRIPTION OF THE INVENTION

Figure 1:
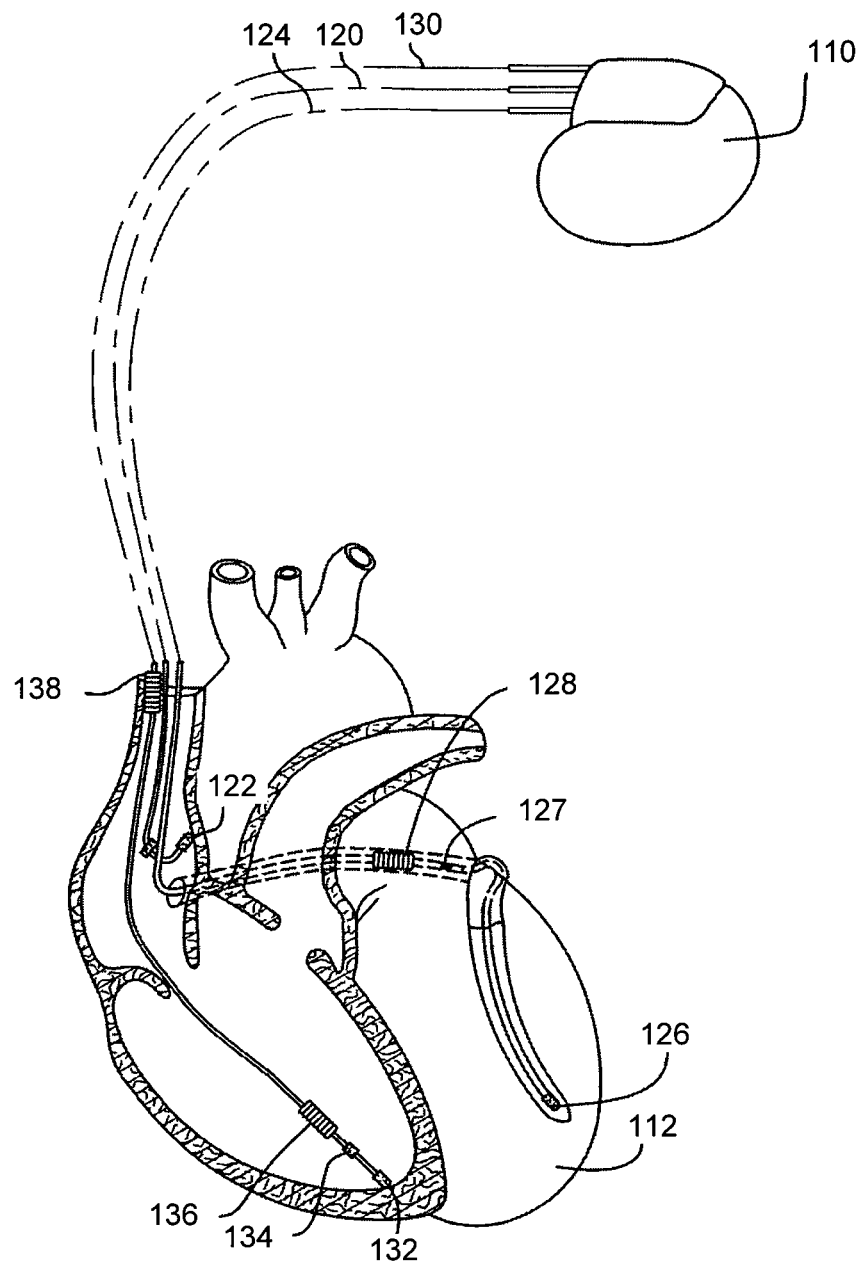
FIG. 1 is a simplified, partly cutaway view illustrating an exemplary implantable cardiac stimulation device in electrical communication with at least three leads implanted into a patient's heart for delivering multi-chamber stimulation and shock therapy.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

It would be apparent to one of skill in the art reading this description that the various embodiments of the present invention, as described below, may be implemented in many different embodiments of hardware, software, firmware, and/or the entities illustrated in the Figures. Any actual software, firmware and/or hardware described herein is not limiting of the present invention. Thus, the operation and behavior of the embodiments of the present invention will be described with the understanding that modifications and variations of the embodiments are possible, given the level of detail presented herein.

Exemplary Implantable Cardiac Stimulation Device

FIG. 1 illustrates an exemplary cardiac stimulation device 110 in electrical communication with a patient's heart 112 by way of three leads 120, 124 and 130 suitable for sensing cardiac electrogram signals and also delivering multi-chamber stimulation and shock therapy. To sense atrial cardiac signals and to provide right atrial chamber stimulation therapy, the cardiac stimulation device 110 is coupled to an implantable right atrial lead 120 having at least an atrial tip electrode 122, which typically is implanted in the patient's right atrial appendage. To sense left atrial and ventricular cardiac signals and to provide left-chamber pacing therapy, the cardiac stimulation device 110 is coupled to a "left ventricular" lead 124 designed for placement in the "left ventricular region" via the coronary sinus so as to place distal electrode(s) adjacent to the left ventricle and additional electrode(s) potentially adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, the coronary sinus lead 124 is designed to receive atrial and ventricular cardiac signals and to deliver left ventricular pacing therapy using at least a left ventricular tip electrode 126, left atrial pacing therapy using at least a left atrial ring electrode 127, and shocking therapy using at least a left atrial coil electrode 128.

The cardiac stimulation device 110 is also shown in electrical communication with the patient's heart 112 by way of an implantable right ventricular lead 130 having, in this embodiment, a right ventricular tip electrode 132, a right ventricular ring electrode 134, a right ventricular (RV) coil electrode 136, and an SVC coil electrode 138. Typically, the right ventricular lead 130 is transvenously inserted into the heart 112 so as to place the right ventricular tip electrode 132 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals, and delivering stimulation in the form of pacing and shock therapy to the right ventricle. As will be appreciated from the discussion below, MELs, such as but not limited to the MELs discussed with reference to FIGS. 4A-4C, can be used in place of the more conventional leads 120, 124 and/or 130 shown in FIG. 1.

Figure 2A:
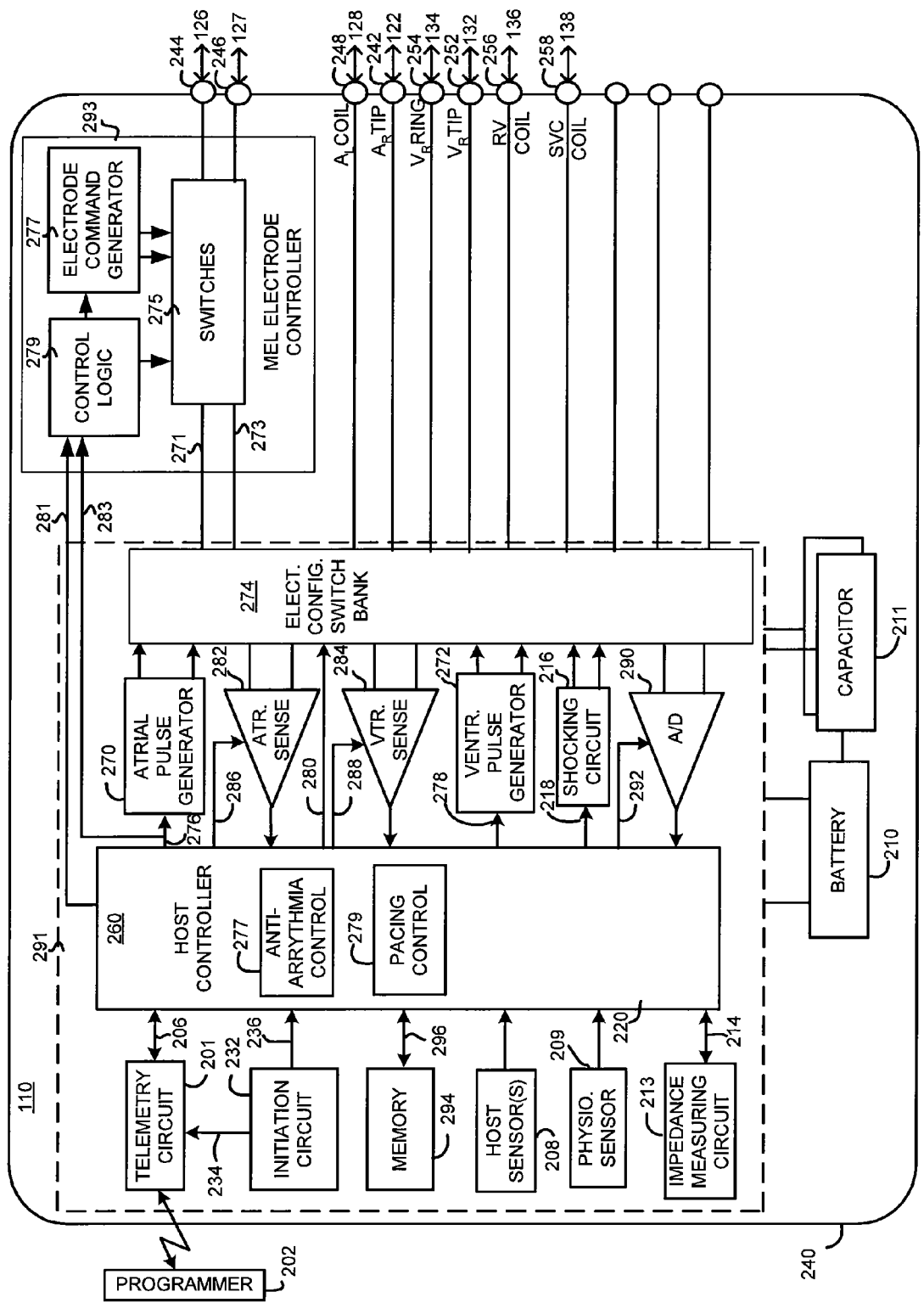
FIG. 2A is a functional block diagram of the exemplary multi-chamber implantable cardiac stimulation device of FIG. 1, illustrating a MEL electrode controller, as well as, the basic elements that provide cardioversion, defibrillation and/or pacing stimulation in four chambers of the heart.

FIG. 2A illustrates a simplified block diagram of the multi-chamber implantable cardiac stimulation device 110 which is capable of sensing cardiac electrogram signals, and also treating both fast and slow arrhythmias with stimulation therapy, including cardioversion, defibrillation, pacing stimulation. While a particular multi-chamber cardiac stimulation device is shown, this is for illustration purposes only and one of skill in the art could readily duplicate, eliminate or disable the appropriate circuitry in any desired combination to provide a device capable of sensing cardiac electrogram signals, treating the appropriate chamber(s) with cardioversion, defibrillation and/or pacing stimulation without departing from the scope of the invention.

Referring to FIG. 2A, cardiac stimulation device 110 includes a housing 240 which is often referred to as a "can", "case" or "case electrode", and which may be programmably selected to act as the return electrode for all "unipolar" modes. Housing 240 may be used as a return electrode alone or in combination with one or more of the coil electrodes 128, 136, or 138, for shocking purposes. Housing 240 further includes a connector (not shown) having a plurality of terminals, 242, 244, 246, 248, 252, 254, 256, and 258 (shown schematically and, for convenience, the names of the exemplary electrodes to which they are connected are shown next to the terminals).

To achieve right atrial sensing and pacing, the connector includes at least a right atrial tip terminal 242 adapted for connection to the right atrial (AR) tip electrode 122. To support right chamber sensing, pacing and/or shocking, the connector further includes a right ventricular (VR) tip terminal 252, a right ventricular (VR) ring terminal 254, a right ventricular (RV) shocking terminal (coil) 256, and an SVC shocking terminal (coil) 258, which are adapted for connection to the right ventricular tip electrode 132, right ventricular ring electrode 134, the RV coil electrode 136, and the SVC coil electrode 138, respectively. To support left chamber sensing, pacing (and/or optionally shocking), the connector can include a left ventricular (VL) tip terminal 244, a left atrial (AL) ring terminal 246, and optionally a left atrial (AL) shocking terminal (coil) 248, which are adapted for connection to the left ventricular tip electrode 126, the left atrial ring electrode 127, and the left atrial coil electrode 128, respectively. As mentioned above (and described in more detail below), MELs, such as but not limited to the MELs discussed with reference to FIGS. 4A-4C, can be used in place of the more conventional leads 120, 124 and/or 130 shown in FIG. 1. Where a MEL is being used, as few as two terminals can be used for each MEL (e.g., one terminal for each conductor of a bus of the MEL).

At the core of cardiac stimulation device 110 is a programmable microcontroller, host controller 260, which controls the various modes of stimulation therapy. As is well known in the art, host controller 260 can include a microprocessor, or equivalent control and switching circuitry or processor, designed for controlling the delivery of stimulation therapy, and may further include Random Access Memory (RAM) or Read Only Memory (ROM) memory, logic and timing circuitry, state machine circuitry, and I/O circuitry. Typically, host controller 260 includes the ability to process or monitor input signals (data) as controlled by program code stored in a designated block of memory. The details of the design and operation of host controller 260 are not critical to the present invention. Rather, any suitable host controller 260 may be used that carries out the functions described herein. The use of microprocessor-based control circuits for performing timing and data analysis functions is well known in the art.

As shown in FIG. 2A, an atrial pulse generator 270 and a ventricular pulse generator 272 generate pacing stimulation pulses for delivery by the right atrial lead 120, the right ventricular lead 130, and/or the coronary sinus lead 124 via a switch bank 274. It is understood that in order to provide stimulation therapy in each of the four chambers of the heart, the atrial pulse generator 270 and the ventricular pulse generator 272 may include dedicated, independent pulse generators, multiplexed pulse generators, or shared pulse generators. The atrial pulse generator 270 and the ventricular pulse generator 272 are controlled by host controller 260 via appropriate control signals 276 and 278, respectively, to trigger or inhibit the stimulation pulses. In an embodiment, the atrial pulse generator 270 and the ventricular pulse generator 272 are adapted to generate stimulation pulses that are delivered via a MEL.

Host controller 260 further includes pacing control unit 279 which is used to control the timing of such stimulation pulses (e.g., pacing rate, atrioventricular (AV) delay, atrial interconduction (AA) delay, ventricular interconduction (VV) delay, pacing mode, etc.), as well as to keep track of the timing of refractory periods, PVARP intervals, noise detection windows, evoked response windows, alert intervals, marker channel timing, etc.

The switch bank 274 includes a plurality of electrically configurable switches for connecting the desired electrodes to the appropriate I/O circuits, thereby providing complete electrode programmability. Accordingly, the switch bank 274, in response to a control signal 280 from host controller 260, determines the polarity of the stimulation pulses (e.g., unipolar, bipolar, combipolar, etc.) by selectively closing the appropriate combination of switches (not shown) as is known in the art. If multiple RV electrodes are employed to generate a single averaged ventricular signal, then switch bank 274 is configured to allow the paralleling (or averaging) of the multiple RV electrodes to simulate a large electrode for accurate sensing of the T-wave. Alternatively (or additionally) each group of electrodes of a MEL can include its own switching circuitry, as described in more detail below.

Atrial sensing circuits 282 and ventricular sensing circuits 284 may also be selectively coupled to the right atrial lead 120, coronary sinus lead 124, and the right ventricular lead 130, through the switch bank 274, for detecting the presence of cardiac activity in each of the four chambers of the heart. Accordingly, the atrial and ventricular sensing circuits 282 and 284 may include dedicated sense amplifiers, multiplexed amplifiers, or shared amplifiers. The switch bank 274 can determine the "sensing polarity" of the cardiac signal by selectively closing the appropriate switches. In this way, the clinician may program the sensing polarity independent of the stimulation polarity. Each of the sensing circuits, 282 and 284 preferably employ one or more low power, precision amplifiers with programmable gain and/or automatic gain control, bandpass filtering, and a threshold detection circuit, to selectively sense the cardiac signal of interest. The automatic gain control enables the cardiac stimulation device 110 to deal effectively with the difficult problem of sensing the low amplitude signal characteristics of atrial or ventricular fibrillation.

The outputs of the atrial and ventricular sensing circuits 282 and 284 are connected to host controller 260 for triggering or inhibiting the atrial and ventricular pulse generators 270 and 272, respectively, in a demand fashion, in response to the absence or presence of cardiac activity, respectively, in the appropriate chambers of the heart. The atrial and ventricular sensing circuits 282 and 284, in turn, receive control signals over signal lines 286 and 288 from host controller 260, for controlling the gain, threshold, polarization charge removal circuitry (not shown), and the timing of any blocking circuitry (not shown) coupled to the inputs of the atrial and ventricular sensing circuits 282 and 284.

Cardiac signals are also applied to the inputs of an analog-to-digital (A/D) data acquisition system 290. Data acquisition system 290 is configured to acquire intracardiac electrogram signals, convert the raw analog data into digital signals, and store the digital signals for later processing and/or telemetric transmission to an external device 202. Data acquisition system 290 is coupled to the right atrial lead 120, the coronary sinus lead 124, and the right ventricular lead 130 through switch bank 274 to sample cardiac signals across any pair of desired electrodes. Data acquired by data acquisition system 290 (and optionally stored) can be used for subsequent analysis to guide the programming of the device, appropriately adjust pacing interval parameters, select optimum pacing intervals, and/or select appropriate anti-arrhythmia therapy.

Advantageously, data acquisition system 290 may be coupled to host controller 260 or other detection circuitry, for detecting an evoked response from the heart 112 in response to an applied stimulus, thereby aiding in the detection of "capture". Capture occurs when an electrical stimulus applied to the heart is of sufficient energy to depolarize the cardiac tissue, thereby causing the heart muscle to contract. Host controller 260 detects a depolarization signal during a window following a stimulation pulse, the presence of which indicates that capture has occurred. Host controller 260 enables capture detection by triggering the ventricular pulse generator 272 to generate a stimulation pulse, starting a capture detection window using the timing circuitry within host controller 260, and enabling data acquisition system 290 via control signal 292 to sample the cardiac signal that falls in the capture detection window and, based on the amplitude of the sampled cardiac signal, determines if capture has occurred.

One function of the cardiac stimulation device 110 can be to operate as an implantable cardioverter/defibrillator ("ICD") device. That is, cardiac stimulation device 110 detects the occurrence of an arrhythmia, and automatically applies an appropriate electrical shock therapy to the heart aimed at terminating the detected arrhythmia. To this end, anti-arrhythmia control unit 277 of control host controller 260 further controls a shocking circuit 216 by way of a control signal 218. The shocking circuit 216 generates shocking pulses of low (up to 0.5 joules), moderate (0.5-10 joules), or high (11-40 joules) energy, as controlled by host controller 260. Such shocking pulses are applied to the patient's heart through at least two shocking electrodes, as shown in this embodiment, selected from the left atrial coil electrode 128, the RV coil electrode 136, and/or the SVC coil electrode 138 (FIG. 1). As noted above, the housing 140 may act as an active electrode in combination with the RV electrode 136, or as part of a split electrical vector using the SVC coil electrode 138 or the left atrial coil electrode 128 (e.g., using the RV electrode as a common electrode). The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

For arrhythmia detection, an anti-arrhythmia control unit 277 of host controller 260 utilizes the atrial and ventricular sensing circuits 282 and 284 to sense cardiac signals, for determining whether a rhythm is physiologic or pathologic. The timing intervals between sensed events (e.g., P-waves, R-waves, and depolarization signals associated with fibrillation which are sometimes referred to as "F-waves" or "Fib-waves") are then classified by anti-arrhythmia control unit 277 of host controller 260 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Host controller 260 is further coupled to a memory 294 by a suitable data/address bus 296, where the programmable operating parameters used by host controller 260 are stored and modified, as required, in order to customize the operation of the cardiac stimulation device 110 to suit the needs of a particular patient. Such operating parameters define, for example, pacing pulse amplitude, pulse duration, electrode polarity, rate, sensitivity, automatic features, arrhythmia detection criteria, pacing mode, and the amplitude, waveshape and vector of each shocking pulse to be delivered to the patient's heart 112 within each respective tier of therapy. A feature of the cardiac stimulation device 110 is the ability to sense and store a relatively large amount of data (e.g., from data acquisition system 290), which data may then be used for subsequent analysis and also guiding the programming of the cardiac stimulation device 110. The host controller 260 can also be connected to host sensor(s) 208, a physiologic sensor 209, and an impedance measuring circuit 213, as shown.

Advantageously, the operating parameters of the cardiac stimulation device 110 may be non-invasively programmed into the memory 294 through a telemetry circuit 201 in telemetric communication with an external programmer 202, such as a transtelephonic transceiver, or a diagnostic system analyzer. Additionally, telemetry circuit 201 may be used to guide the device 110 through electrode set-up algorithms.

A handshake signal can be sent from the programmer 202 (or other external device) to the telemetry circuit 201 so that the external device can be identified to the telemetry circuit 201 thereby defining what operations may be performed by the device. The programmer 202 can program the cardiac stimulation device 110 under the control of a physician as described in more detail with respect to FIG. 3. For examples of such programmers, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (this relates to transfer of EGM data) (McClure et al.), which patents are hereby incorporated herein by reference.

Cardiac stimulation device 110 further includes initiation circuit 232. Initiation circuit 232 may comprise magnet detection circuitry. Initiation circuit 232 is coupled to host controller 260 by connection 236 and/or to telemetry circuit 201 by connection 234. The purpose of the initiation circuit is to detect an initiation signal from outside the patient. For example, a magnet placed over the cardiac stimulation device 110 may be used as the initiation signal, which signal may be used by a clinician to initiate various test functions of the cardiac stimulation device 110 and/or to signal host controller 260 that an external programmer 202 is in place to receive or transmit data to host controller 260 through the telemetry circuit 201. Initiation circuit 232 may also be used to activate electrode set-up algorithms.

Host controller 260 can process electrogram (EGM) signals to monitor for capture during pacing and to measure R-waves during sensing.

Figure 2B:
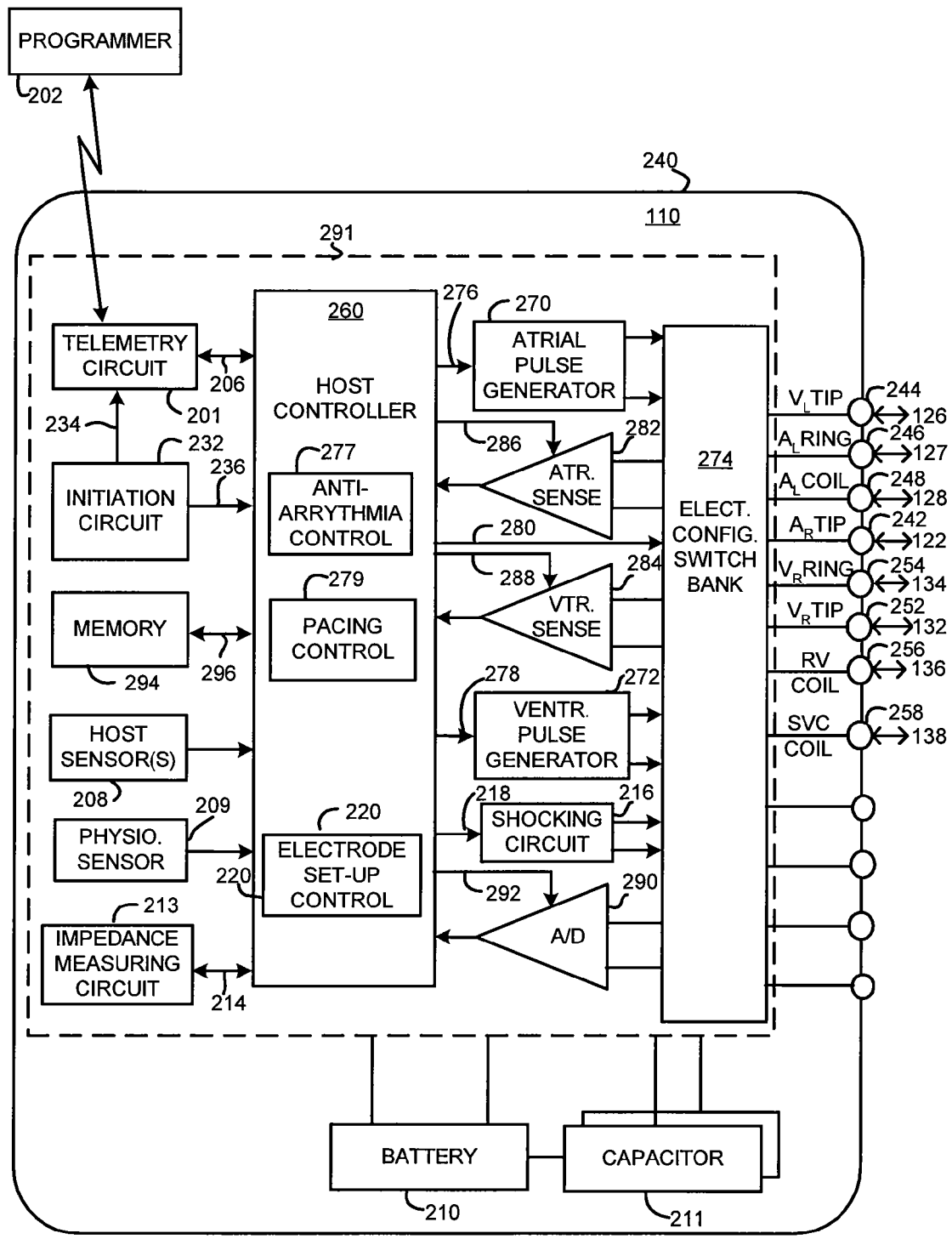
FIG. 2B is a functional block diagram of an alternate multi-chamber implantable cardiac stimulation device wherein the functions of the MEL electrode controller are performed in the same chip that controls the pacing and sensing.

Cardiac stimulation device 110 additionally includes a power source such as a battery 210 that provides operating power to all the circuits shown in FIGS. 2A and 2B. For a cardiac stimulation device 110, which employs shocking therapy, the battery 210 should be capable of operating at low current drains for long periods of time and also be capable of providing high-current pulses (for charging capacitor 211) when the patient requires a shock pulse. Battery 210 must preferably have a predictable discharge characteristic so that elective replacement time can be detected. Accordingly, cardiac stimulation device 110 can employ lithium/silver vanadium oxide batteries.

Where a MEL is connected to the cardiac stimulation device, a controller can be used to send one or more commands to control circuitry of the MEL to set up and refresh the electrode configuration of the MEL. Exemplary controllers can include a MEL electrode controller 293 shown in FIG. 2A, or an electrode set up control 220 shown in FIG. 2B. The controller can be used to send the one or more commands as shown in the timing diagram of FIG. 5 possibly under the control of an external device (e.g., an external programmer 202). Additionally, the controller can also configure electrodes in specific configurations, possibly as instructed by an external device, such as the external programmer 202. The controller, such as MEL electrode controller 293 or electrode set up control 220, can include software, firmware, hardware or combinations thereof.

A MEL can be used in place of the conventional coronary sinus lead 124 shown in FIG. 1, and thus, to sense left atrial and ventricular cardiac signals and to provide left-chamber pacing therapy. Additionally, or alternatively, a MEL can be used in place of the right atrial lead 120 and/or the right ventricular lead 130.

As shown in FIG. 2A, a MEL electrode controller 293 can be connected to receive signals from the switch bank 274 via lines 271 and 273. The MEL controller 293 is shown as including switches 275, control logic 279 and an electrode command generator 277. The switches 275 can be used to connect and disconnect pacing and sensing circuitry (e.g., 270, 272, 282 and/or 284) at the appropriate times, and to switch in one or more commands generated by the MEL command generator 277. The MEL command generator 277 can produce commands that are to be sent to the control circuitry of a MEL.

In one embodiment, the host controller 260 can send command signals on line 281 to control logic 279 to indicate what commands are to be sent to the control circuitry at a MEL.

As will be discussed in more detail below, with reference to FIG. 5, each pacing pulse produced by the pulse generators 270 and 272 can include a primary pace pulse portion followed by an initial change balancing portion. An indication of the initiation of a primary pace pulse portion can be received on line 283 from the host controller 260. In one embodiment, this is a "PGRANT" signal sent to the atrial pulse generator 270. Alternatively, the MEL electrode controller 293 can monitor (e.g., snoop) lines 271 and 273 to detect a specific feature (e.g. the leading or falling edge) of the primary pace pulse portion. After the indication on line 283 is received, or a specific feature of the primary pacing pulse is detected, one or more commands can be sent to control circuiting within a MEL.

FIG. 2B shows an example embodiment where the host controller 260 includes MEL electrode control logic 220 that can be used to create the commands that are sent to control circuitry of a MEL. In this embodiment, the commands can then be sent through the switch bank 274 to the control circuitry of the MEL. Depending on the desired electrical qualities of the commands, a separate MEL command generator (not shown) connected to host controller 260 can also be used.

Exemplary Programmer

Figure 3:
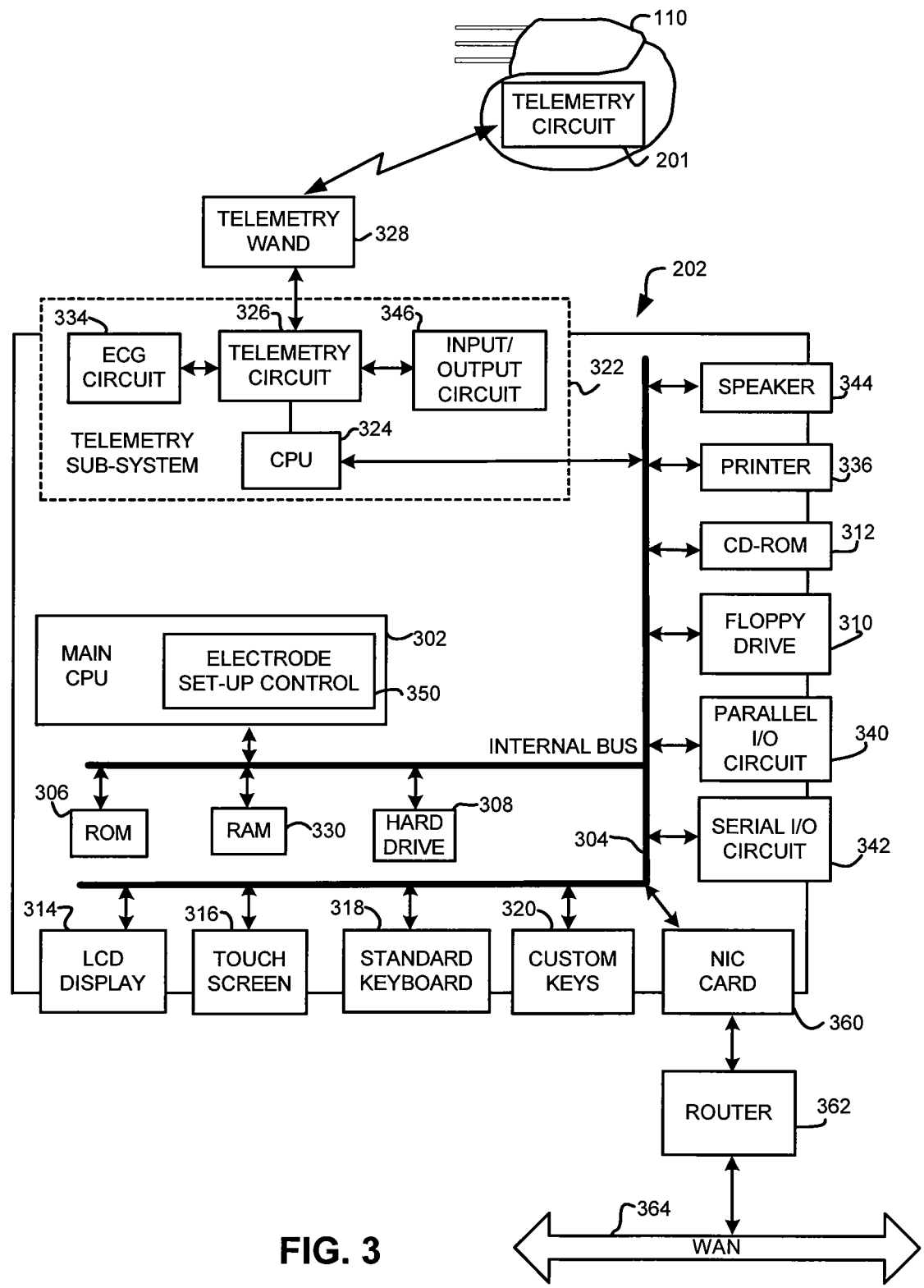
FIG. 3 is a functional block diagram illustrating components of an exemplary programmer for use in programming the implantable cardiac stimulation device of FIGS. 1 and 2A-2B.

FIG. 3 illustrates components of an exemplary programmer 202 for use in programming an implantable cardiac stimulation device, including setting up electrode configurations of an implantable cardiac stimulation device. The programmer 202 permits a physician or other authorized user to program the operation of the implantable cardiac stimulation device 110 and to retrieve and display information received from the implantable cardiac stimulation device 110 such as EGM data and device diagnostic data. Additionally, the programmer 202 may receive and display electrocardiogram (ECG) data from separate external ECG leads that may be attached to the patient. Further, the programmer 220 is capable of causing the implantable cardiac stimulation device to perform functions necessary to complete certain electrode set-up algorithms of the present invention. Depending upon the specific programming of the programmer, programmer 202 may also be capable of processing and analyzing data received from the implantable cardiac stimulation device 110 and from ECG leads to, for example, render preliminary diagnosis as to medical conditions of the patient or to the operations of the implantable cardiac stimulation device 110.

Now, considering the components of the programmer 202 by reference to FIG. 3, operations of the programmer 202 can be controlled by a Central Processing Unit (CPU) 302, which may be a generally programmable microprocessor or microcontroller or may be a dedicated processing device such as an Application Specific Integrated Circuit (ASIC) or the like. Software instructions to be performed by the CPU can be accessed via an internal bus 304 from a Read Only Memory (ROM) 306 and Random Access Memory (RAM) 330. Additional software may be accessed from a hard drive 308, floppy drive 310, and CD ROM drive 312, or other suitable permanent mass storage device. Depending upon the specific implementation, a Basic Input Output System (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 314 or other suitable computer display device. To this end, the CPU may, for example, display a menu of specific programming parameters of the implantable cardiac stimulation device 110 to be programmed or may display a menu of types of diagnostic data to be retrieved and displayed. In response thereto, the physician enters various commands via either a touch screen 316 overlaid on LCD display 314 or through a standard keyboard 318 supplemented by additional custom keys 320, such as an emergency VVI (EVVI) key. The EVVI key sets the implantable cardiac stimulation device 110 to a safe VVI mode with high pacing outputs. This ensures life-sustaining pacing operation in nearly all situations but by no means is it desirable to leave cardiac stimulation device 110 in the EVVI mode at all times.

Typically, the physician initially controls the programmer 202 to retrieve data stored within the implanted medical device and to also retrieve ECG data from ECG leads (examples discussed above with reference to FIGS. 1 and 2) coupled to the patient's myocardium. To this end, CPU 302 transmits appropriate signals to a telemetry circuit 322, which provides components for directly interfacing with implantable cardiac stimulation device 110. The telemetry subsystem 322 can include its own separate CPU 324 for coordinating the operations of the telemetry subsystem 322. The main CPU 302 of the programmer 202 communicates with telemetry subsystem CPU 324 via internal bus 304. The telemetry subsystem 322 additionally includes a telemetry circuit 326 connected to a telemetry wand 328, which cooperate to receive and transmit signals electromagnetically from telemetry circuit 201 of the implantable cardiac stimulation device 110. The telemetry wand 328 is placed over the chest of the patient near the implanted cardiac stimulation device 110 to permit reliable transmission of data, over telemetric link 205, between the telemetry wand and the implantable cardiac stimulation device 110. Typically, at the beginning of the programming session, the external programming device controls the implantable cardiac stimulation device 110 via appropriate signals generated by telemetry wand 328 to output all previously recorded patient and device diagnostic information. Patient diagnostic information includes, for example, measured physiological variables data, recorded EGM data and statistical patient data such as the percentage of paced versus sensed heartbeats. Device diagnostic data includes, for example, information representative of the operation of the implantable cardiac stimulation device 110 such as lead impedances, battery voltages, battery Recommended Replacement Time (RRT) information and the like. Data retrieved from the implantable cardiac stimulation device 110 is stored by the external programmer 202 either within a RAM 330, a hard drive 308, within a floppy diskette placed within a floppy drive 310, etc. Additionally, or in the alternative, data may be permanently or semi-permanently stored within a Compact Disk (CD) or other digital media disk, if the overall system is configured with a drive for recording data onto digital media disks, such as a Write Once Read Many (WORM) drive.

Patient and device diagnostic data stored within the implantable cardiac stimulation device 110 can be transferred to the programmer 202. Further, the implantable cardiac stimulation device 110 can be instructed to perform an electrode set-up algorithm of the present invention, details of which are provided below.

The programmer 202 can also include a Network Interface Card ("NIC") 360 to permit transmission of data to and from other computer systems via a router 362 and Wide Area Network ("WAN") 364. Alternatively, the programmer 202 might include a modem for communication via the Public Switched Telephone Network (PSTN). Depending upon the implementation, the modem may be connected directly to internal bus 304 and may be connected to the internal bus via either a parallel port 340 or a serial port 342. Data transmitted from other computer systems may include, for example, data regarding medication prescribed, administered or sold to the patient.

The CPU 302 can include an electrode set-up control 350 that can control the performance of the steps 502 and 504 described below with reference to FIG. 5, and/or instruct the implantable stimulation device 110 to perform such steps. The electrode set-up control 350 of CPU 302 can operate in concert with the electrode set-up control 220 or 293 of device 110, or independent thereof. The programmer 202 receives data from the implantable cardiac stimulation device 110, including parameters representative of the current programming state of the implantable cardiac stimulation device 110. Under the control of the physician, programmer 202 displays the current programming parameters and permits the physician to reprogram the parameters. To this end, the physician enters appropriate commands via any of the aforementioned input devices and, under control of the CPU 302, the programming commands are converted to specific programming parameters for transmission to the implantable cardiac stimulation device 110 via the telemetry wand 328 to thereby reprogram the implantable cardiac stimulation device 110. Prior to reprogramming specific parameters, the physician may control the external programmer to display any or all of the data retrieved from the implantable cardiac stimulation device 110, including displays of ECGs, displays of electrodes that are candidates as cathodes and/or anodes, and statistical patient information. Any or all of the information displayed by programmer 202 may also be printed using a printer 336.

A speaker 344 is included for providing audible tones to the user, such as a warning beep in the event improper input is provided by the physician. Telemetry subsystem 322 may additionally include an input/output circuit 346 which can control the transmission of analog output signals, such as ECG signals output to an ECG machine or chart recorder. Other peripheral devices may be connected to the external programmer 202 via parallel port 340 or a serial port 342 as well. Although one of each is shown, a plurality of Input Output (10) ports might be provided.

With the programmer 202 configured as shown, a physician or other authorized user can retrieve, process and display a wide range of information received from the implantable cardiac stimulation device 110 and reprogram the implantable cardiac stimulation device 110, including configurations of leads, if needed. The descriptions provided herein with respect to FIG. 3 are intended merely to provide an overview of the operation of the exemplary programmer 202 and are not intended to describe in detail every feature of the hardware and software of the device and are not intended to provide an exhaustive list of the functions performed by the device.

Exemplary Multi-Electrode Leads

Figure 4A:
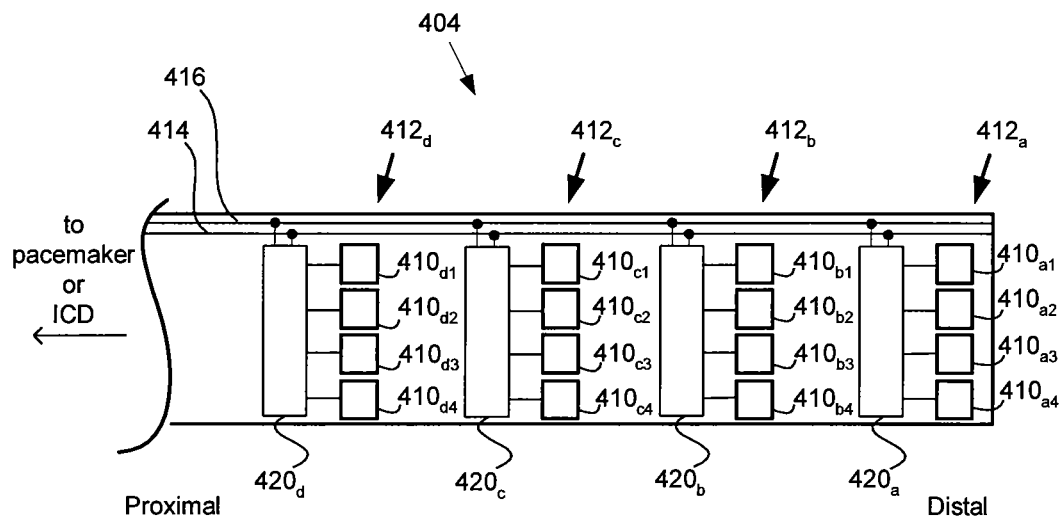
FIGS. 4A-4C schematically illustrates portions of exemplary Multi-Electrode Leads with which embodiments of the present invention can be useful.

FIG. 4A illustrates a portion of an exemplary MEL 404, which can be used with specific embodiments of the present invention. While not specifically shown in FIG. 4A, the lead 404 can be connected to the implantable cardiac stimulation device 110, e.g., in place of any of leads 120, 124 and/or 130. For the purpose of the following description, the lead 404 will be described as having a 4×4 matrix of electrodes, because the lead includes four arrays (also referred to as groups or bands) of electrodes, each of which includes four electrodes 410. Each electrode 410 is electrically isolated from the other electrodes 410, but is capable of being electrically connected to other electrodes. Thus, exemplary lead 404 includes sixteen electrically isolated electrodes 410.

In accordance with an embodiment, electrodes within the same group share at least some common control and switching circuitry. Further, in accordance with an embodiment, electrodes within a same group are within 5 mm of one another, while electrodes within different groups are at least 10 mm from one another.

Figure 4B:
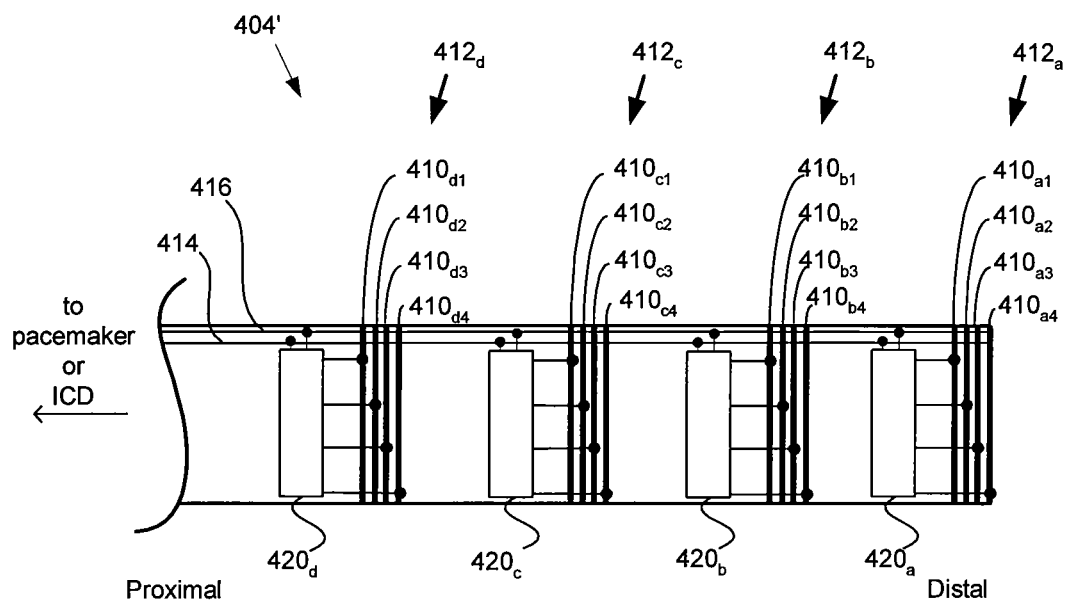
Figure 4C:
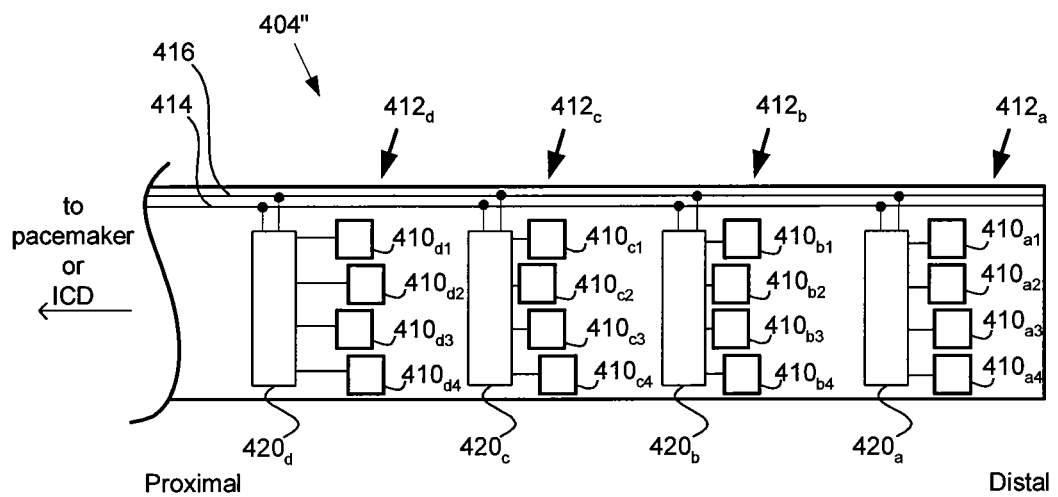

As shown in FIG. 4A, a first group of electrodes $412_a$, which is most distal from the implantable cardiac stimulation device 110, includes electrodes $410_{a1}$, $410_{a2}$, $410_{a3}$ and $410_{a4}$. A second group of electrodes $412_b$, which is more proximal to the implantable cardiac stimulation device 110, includes electrodes $410_{b1}$, $410_{b2}$, $410_{b3}$ and $410_{b4}$. Also shown are a third group of electrodes $412_c$ and a fourth group of electrodes $412_d$, including electrodes $410_{c1}$-$410_{c4}$ and $410_{d1}$-$410_{d4}$, respectively. The groups of electrodes are shown schematically, and are not drawn to scale. For example, it may be that each electrode 410, of a group of electrodes 412, actually occupies slightly less than 90 degrees of a ring around a lead. Alternatively, electrodes 412 of a group 410 can be a very closely spaced ring electrodes, e.g., as shown in FIG. 4B. FIG. 4C shows yet another example of groups 412 of electrodes 410. Other groups of electrodes are also possible, as one of ordinary skill in the art would appreciate from this description.

Each MEL (e.g., 404) is also shown as including conductors 414 and 416, which can collectively be referred to as a communication bus. It is also possible that such a bus can include more than two conductors.

Also, as shown in FIG. 4A, the first group of electrodes $412_a$ is connected to control and switching circuitry $420_a$. The second group of electrodes $412_b$ is connected to control and switching circuitry $420_b$. Also shown are a third group of electrodes 412 and a fourth group of electrodes $412_d$, which are connected to control circuitries $412_c$ and $412_d$, respectively.

The control and switching circuitry 420 enables multiple electrodes to be selectively connected to the conductors 414 and 416. Signals can be sent via the conductors 414 and 416 from the implantable cardiac stimulation device 110 to the control and switching circuitry $420_a$-$420_d$, and to control which electrode(s) in groups $412_a$-$412_d$ are to be connected to the conductors 414 and 416. The same conductors 414 and 416 (or alternate conductors) can be used to deliver stimulation pulses to the various electrodes for pacing and/or optionally shocking a patient's heart, and for sensing cardiac signals.

In accordance with an embodiment, the control and switching circuitry 420 associated with each group of electrodes can include, e.g., a shift register for shifting in bits of the communications sequences and/or a latch for latching bits of the communications sequences. Additionally, the control and switching circuitry 420 associated with each group of electrodes can include logic circuitry (e.g., a state machine, but not limited thereto) that can count wait states, identify which bits are intended for use by the group of electrodes and/or can identify the operation designated by an op-code (e.g., can identify whether an anode configuration or a cathode configuration is to be configured). The control and switching circuitry 420 associated with each group of electrodes can also include, or have associated with it, a charge pump for generating a voltage sufficient to power the control and switching circuitry 420 based on signals received via the conductors 414 and 416 (or alternate conductors) from the implantable cardiac stimulation device 110. The control and switching circuitry 420 can also include switches (e.g., transistor switches) that are controlled to configure specific electrodes of a group of electrodes, as an anode, a cathode, or as neither an anode nor cathode.

Another example of a MEL is disclosed, for example, in U.S. Patent Publication No. 2006/0058588 (U.S. patent application Ser. No. 11/219,305), entitled "Methods and Apparatus for Tissue Activation and Monitoring" (Zdeblick), published Mar. 16, 2006 (filed Sep. 1, 2005), which is incorporated herein by reference above (referred to hereafter as "the '588 patent publication"). MELs of the '588 patent publication include what are referred to as "satellites", where each satellite essentially includes a group of electrodes with control and switching circuitry that enables any electrode of a group to be connected to one of two conductors. Stated another way, each group of electrodes can be said to include control and switching circuitry. Such control and switching circuitry is controlled by a controller associated with a cardiac stimulation device (e.g., pacemaker and/or ICD), to which the lead is attached. Digital signals can be sent via the two conductors from the controller to the control and switching circuitry, to thereby control which electrode(s) is/are to be connected to which of the two conductors. Additionally, analog signals can be sent via the two conductors between the pacemaker and electrodes for delivering pacing pulses and sensing. The '588 patent publication discloses that one such lead can include, e.g., eight satellites, with each satellite comprising four electrodes, which would result in a lead having thirty-two electrodes. The electrodes of the leads 404, 404' and 404" of FIGS. 4A-4C can be configured and controlled in a similar manner as those disclosed in the '588 patent publication.

FIGS. 4A-4C discussed above illustrate exemplary leads 404, 404' and 404" that each has four groups of electrodes, with each group of electrodes comprising four electrodes, resulting in each lead having a total of sixteen electrodes. Such leads can be used to implement embodiments of the present invention. When using a lead such as those in FIGS. 4A-4C, the cathode can be one or more electrode in a group, and the anode can be one or more electrode of that same group (which may, or may not be electrically connected with one or more electrode of another group). However, embodiments of the present invention are not limited to use with MELs that are similar to those described with reference to FIGS. 4A-4C. Rather, certain embodiments of the present invention can be used with any lead that includes multiple groups of electrodes, including those disclosed in the '588 patent publication.

These are just a few examples of MELs with which embodiments of the present invention can be used. However, embodiments of the present invention, unless stated otherwise, are not limited to use with the exemplary leads described herein.

Exemplary protocols for configuring a MEL are described in U.S. patent application Ser. No. 12/537,936, filed Aug. 7, 2009 and entitled "Systems and Methods to Configure a Multi-Electrode Lead", which is incorporated herein by reference.

It is possible that electrodes of different groups of electrodes are configured as an anode at the same time, which can be used to provide a "distributed" anode configuration. Benefits of using what is referred to as a "distributed" anode configuration, where one electrode of the anode is within the same group as the cathode electrode(s), but another electrode of the anode is in a different group than the cathode electrode(s), are discussed in commonly assigned U.S. patent application Ser. No. 11/688,941, entitled "Distributed Anode Cardiac Pacing and Sensing", filed Mar. 21, 2007 (Shelchuk), which is incorporated herein by reference. Embodiments of the present invention contemplate the use of a distributed anode. It is also possible that electrodes of different groups of electrodes are configured as a cathode at the same time.

Timing of MEL Commands

In prior systems, commands sent to control circuitry within a MEL were not synchronized with pacing pulses. For example, the commands were periodically sent to refresh the control circuitry at the MEL as needed, but this could occur at any point in the pacing cycle. Such unsynchronized commands can potentially undesirably stimulate the heart as well as interfere with pacing and sensing.

Figure 5:
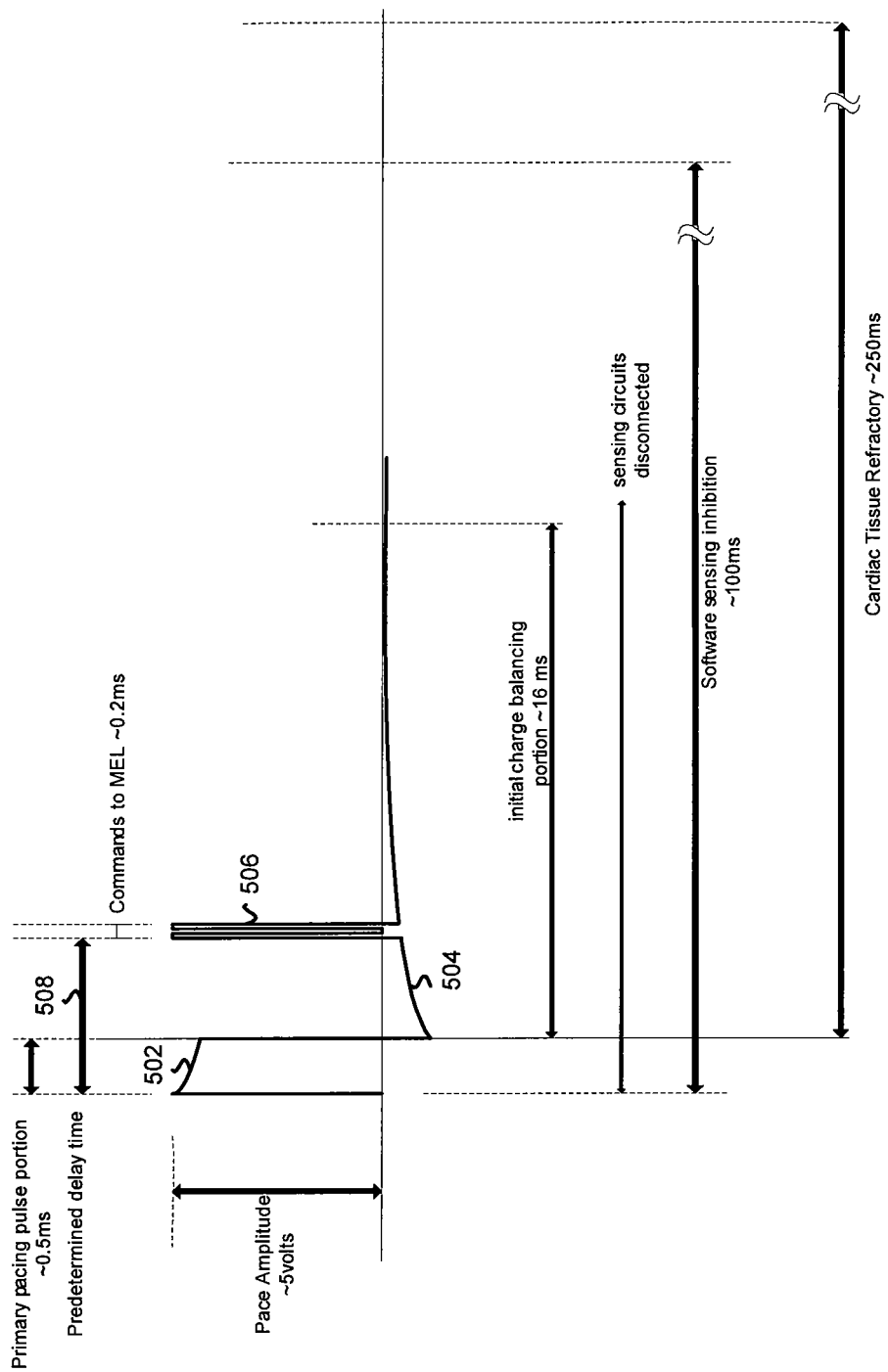
FIG. 5 is a timing diagram of one embodiment of the present invention illustrating the sending of one or more commands to the control circuitry on the MEL within a cardiac pacing cycle.

FIG. 5 shows a timing diagram that illustrates an example of the synchronizing the sending of commands 506 with a pacing cycle, in accordance with an embodiment of the present invention. Such commands 506, as mentioned above, are sent to control circuitry within a MEL. The commands 506 can be used to do one or more of query, change, refresh, or reset to a default, which one or more electrodes, if any, of the MEL is/are configured as an anode and which one or more electrodes of the MEL, if any, is/are configured as a cathodes. The commands can also be used to instruct the MEL to enter or exit a low power mode.

In accordance with an embodiment, the commands 506 are sent during a predetermined portion of a cardiac pacing cycle. More specifically, the one or more commands can be sent when cardiac tissue is refractory from a cardiac pacing pulse, to thereby prevent the commands 506 from potentially undesirably stimulating cardiac tissue. Typically, the primary pace pulse portion 502 can cause the cardiac tissue to become refractory to additional stimulation for a period of about 250 ms. This provides a relatively large window for sending the commands.

As can be appreciated from FIG. 5, a pacing pulse typically includes a primary pace pulse portion 502 followed by an initial charge balancing portion 504. The primary pace pulse portion 502 is used to stimulate the heart to cause capture as part of the stimulation therapy discussed above. The charge balancing portion 504 is used to produce a net-zero current flow across the electrode surface. Charge balancing can involve passing the same, or nearly the same amount, of charge through the tissue as was delivered during the primary pace pulse portion, but in the opposite direction. Not doing so can cause an electrochemical imbalance, which can result in electrode corrosion and potentially tissue damage. Typically, charge balancing is done over a significantly longer period of time than it takes for the primary pace pulse portion, as can be appreciated from FIG. 5.

In some devices, the charge for the primary pace pulse portion is provided by a pacing capacitor (not shown), and the charge for the initial charge balancing portion is provided by a blocking capacitor (not shown).

Some embodiments of the present invention involve the sending of commands to the control circuitry of the MEL within the initial charge balancing portion of the pacing pulse. The initial charge balancing portion can be a "fast discharge" portion in which the charge balancing is done at a relatively fast rate as compared to a later "slow discharge" portion. For example, resistor(s) can be switched in and/or out of a discharge path of a blocking capacitor to distinguish the "fast discharge" portion of a pacing pulse from a "slow discharge" portion.

During the initial charge balancing portion 504 of a cardiac pacing pulse, the cardiac tissue will typically already be refractory from the stimulation of the primary pace pulse portion 502 of the pace pulse which immediately precedes the initial charge balancing portion; hence, tissue capture is not a concern if commands are sent. Further, if commands are sent during the initial charge balancing portion of a cardiac pacing pulse, the efficacy of the primary pace pulse portion 502 would not be disrupted by the interruption of commands being sent to the control circuitry (e.g. 420 in FIGS. 4A-4C) of a MEL. Additionally, the device sense amplifiers of the sensing circuitry (e.g., 282 and/or 284 in FIGS. 2A-2B) can still be disconnected such that the one or more commands will not be detected by the sensing circuitry. Finally, interaction analysis with other signals, such as Pacing Lead Impendence (PLI) measurement within the primary pace pulse portion, is not needed if commands are sent during the initial charge balancing portion of a pacing pulse. Preferably, the sending of the one or more commands 506 begins after an end of the primary pace pulse portion 502 and ends prior to an end of the initial charge balancing portion 504, as shown in FIG. 5.

As shown in FIG. 5, the sending of commands 506 can temporarily interrupt the transfer of charge within the initial charge balancing portion 504. For the purpose of this application, despite this temporary interruption, the sending of commands 506 will be considered to be "within" or "during" the initial charge balancing portion, so long as the commands 506 are sent between the end of the primary pace pulse portion 502 and the end of the initial discharge portion 504.

In one embodiment, the initial charge balancing period can last for about 16 ms after the primary pace pulse portion. During the primary pace pulse period and initial charge balancing, the sensing circuitry can be disconnected to prevent the sensing of these signals. In one embodiment, the sensing software is inhibited for about 100 ms after the primary pace pulse portion even though the sensing circuitry for a portion of this period is re-enabled. This is all shown in FIG. 5.

In one embodiment, to provide the one or more commands in the absence of pacing, a zero volt primary pace pulse portion can be delivered (e.g., when an intrinsic beat is expected or detected) to time the sending of the commands. The zero volt primary pace pulse portion is a primary pace pulse portion with the pulse voltage set to zero volts. The zero volt pace pulse portion can be synchronized the same way as a normal primary pace pulse portion. The zero volt primary pace pulse portion can thus trigger the same timing sequence for sending the commands 504 as is used for normal pacing. This can prevent the commands 506 sent to the MEL from inadvertently causing capture or causing sensing problems, since the commands 506 can be sent when the cardiac tissue is refractory from the natural cardiac pacing.

In accordance with an embodiment, the commands 506 can be sent a predetermined delay 508 after a specified feature of the primary pace pulse portion 502, where the delay 508 can be selected, e.g., such that the commands are always send during an initial charge balancing portion 504 of a cardiac pacing pulse. Such a feature can be the start or end of the primary pace pulse portion 502. In one embodiment, the specified feature is a start of the primary pace pulse portion (such as indicated by the PGRANT signal) and the predetermined delay is selected to send the commands during the initial charge balancing portion. While the duration of the primary pace pulse portion is variable, (for example, from 0.5 to 2.0 ms) and the duration of the initial charge balancing portion is variable (for example, from 4.5 to 16 ms), the predetermined delay can be selected such that the commands are sent within the initial charge balancing portion 504, regardless of the durations of the primary pace pulse portion and the initial charge balancing portion. This is acceptable, because a precise time of sending of the one or more commands during the initial charge balancing portion is not critical.

During the initial charge balancing portion 504 of the cardiac pacing pulse, a pulse generator circuitry (e.g., 270 and/or 272) can be disconnected from a MEL and the MEL can be connected to a controller (e.g., 293 or 220) that is adapted to generate the commands 506 that are to control circuitry within the MEL. Further, the one or more commands 506 can be sent to control circuitry within the MEL between instances when the sensing circuitry 282 is being used to obtain signals (e.g., an IEGM or ECG) indicative of cardiac electrical activity. In this manner, the IEGM or ECG will not be adversely affected by the sending of the commands. More specifically, the sensing circuitry (e.g., 282 and/or 284) can be adapted to be selectively connectable and selectively disconnectable from the MEL (e.g., using either switch bank 274 and/or switches 275). Accordingly, while sending the commands, the sensing circuitry (e.g. 282 and 284) can be disconnected from the MEL or disabled, to thereby prevent the sending of the commands from being detected by the sensing circuits 282.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A method for use by an implantable cardiac stimulation device to which a multi-electrode lead (MEL) is attached, the implantable cardiac stimulation device including
   sensing circuitry adapted to selectively obtain, using electrodes selectively connected to the sensing circuitry, one or more signals indicative of cardiac electrical activity, storage circuitry adapted to store data indicative of at least one of the one or more signals obtained using the sensing circuitry, a controller adapted to generate one or more commands that are to be sent to control circuitry within the MEL attached to the implantable cardiac stimulation device, the control circuitry within the MEL adapted to configure electrodes of the MEL attached to the implantable cardiac stimulation device, and pulse generator circuitry adapted to selectively produce cardiac pacing pulses, wherein the MEL, which is attached to the implantable cardiac stimulation device, comprises a multi-conductor bus that includes two conductors, the method for use when sending one or more commands to the control circuitry within the MEL attached to the implantable cardiac stimulation device, the method comprising:

selectively connecting the sensing circuitry to, and disconnecting the sensing circuitry from, the multi-conductor bus of the MEL; and sending one or more commands, over at least one of the two conductors of the multi-conductor bus of the MEL, to the control circuitry within the MEL, between instances when the sensing circuitry is connected to the multi-conductor bus of the MEL and is being used to obtain the one or more signals indicative of cardiac electrical activity.

2. The method of claim 1, further comprising, prior to the sending step:

using switching circuitry of the implantable cardiac stimulation device to disconnect the sensing circuitry from the two conductors of the multi-conductor bus of the MEL and connect the pulse generator circuitry to the two conductors of the multi-conductor bus of the MEL;

while the sensing circuitry is disconnected from the two conductors of the multi-conductor bus of the MEL and the pulse generator circuitry is connected to the two conductors of the multi-conductor bus of the MEL, using the pulse generator circuitry to produce a cardiac pacing pulse that includes a primary pace pulse portion followed by an initial charge balancing portion and a later charge balancing portion, wherein the charge balancing of the initial charge balancing portion is done at a faster rate than the charge balancing of the later charge balancing portion; and during the initial charge balancing portion of the cardiac pacing pulse, disconnecting the pulse generator circuitry from the two conductors of the multi-conductor bus of the MEL and connecting at least one of the two conductors of the multi-conductor bus of the MEL to the controller that is adapted to generate the one or more commands sent over the multi-conductor bus of the MEL during the sending step.

3. The method of claim 1, wherein each of the cardiac pacing pulses, produced by the pulse generator circuitry, includes a primary pace pulse portion followed by an initial charge balancing portion and a later charge balancing portion, wherein the charge balancing of the initial charge balancing portion is done at a faster rate than the charge balancing of the later charge balancing portion, and the sending step comprises:

sending the one or more commands over the at least one of the two conductors of the multi-conductor bus of the MEL to the control circuitry within the MEL during the initial charge balancing portion of the cardiac pacing pulse.

4. The method of claim 1, wherein the sending step, relative to a cardiac pacing pulse produced by the pulse generator circuitry, begins a predetermined delay after a specified feature of a primary pace pulse portion of the cardiac pacing pulse.

5. The method of claim 1, wherein the one or more commands can be used to do one or more of:

query, change, refresh, or reset to a default, which one or more electrodes, if any, of the MEL is/are configured as an anode and which one or more electrodes of the MEL, if any, is/are configured as a cathode.

6. The method of claim 1, wherein:

the pulse generator circuitry is adapted to produce a cardiac pacing pulse that includes a zero volt primary pace pulse portion; and the sending of the one or more commands is timed relative to the zero volt primary pace pulse portion.

7. The method of claim 1, further comprising sending one or more further commands, over the at least one of the two conductors of the multi-conductor bus of the MEL attached to the implantable cardiac stimulation device, to the control circuitry within the MEL, instructing the MEL to enter or exit a low power mode, between instances when the sensing circuitry is connected to the multi-conductor bus of the MEL and is being used to obtain the one or more signals indicative of cardiac electrical activity.

8. The method of claim 1, wherein at least one of the one or more commands, being sent over the at least one of the two conductors of the multi-conductor bus of the MEL, between instances when the sensing circuitry is connected to the multi-conductor bus of the MEL and is being used to obtain the one or more signals indicative of cardiac electrical activity, is used to at least one of query, refresh, or reset to a default, which one or more electrodes, if any, of the MEL is/are configured as an anode and which one or more electrodes of the MEL, if any, is/are configured as a cathode.

9. An implantable cardiac stimulation device, comprising:

sensing circuitry adapted to selectively obtain, using electrodes selectively connected to the sensing circuitry, one or more signals indicative of cardiac electrical activity;

storage circuitry adapted to store data indicative of at least one of the one or more signals obtained using the sensing circuitry;

pulse generator circuitry adapted to selectively produce cardiac pacing pulses;

switching circuitry adapted to selectively connect and disconnect the sensing circuitry to and from a multi-conductor bus of a multi-electrode lead (MEL) attached to the implantable cardiac stimulation device and selectively connect and disconnect the pulse generator circuitry to and from the multi-conductor bus of the MEL, wherein the multi-conductor bus of the MEL includes two conductors; and a controller adapted to send one or more commands over at least one of the two conductors of the multi-conductor bus of the MEL attached to the implantable cardiac stimulation device, to control circuitry within the MEL attached to the implantable cardiac stimulation device, between instances when sensing circuitry is connected by the switching circuitry to the multi-conductor bus of the MEL and is being used to obtain the one or more signals indicative of cardiac electrical activity.

10. The implantable cardiac stimulation device of claim 9, wherein:

the cardiac pacing pulses produced by the pulse generator circuitry include a primary pace pulse portion followed by an initial charge balancing portion and a later charge balancing portion, wherein the charge balancing of the initial charge balancing portion is done at a faster rate than the charge balancing of the later charge balancing portion; and the controller is adapted to send the one or more commands over the at least one of the two conductors of the multi-conductor bus of the MEL attached to the implantable cardiac stimulation device, to the control circuitry within the MEL, such that the one or more commands begin to be sent after the initial charge balancing portion begins, and the one or more commands are finished being sent prior to the initial charge balancing portion ending.

11. The implantable cardiac stimulation device of claim 9, wherein:

cardiac pacing pulses, produced by the pulse generator circuitry, include a primary pace pulse portion followed by an initial charge balancing portion and a later charge balancing portion, wherein the charge balancing of the initial charge balancing portion is done at a faster rate than the charge balancing of the later charge balancing portion; and the controller is adapted to send the one or more commands, over the at least one of the two conductors of the multi-conductor bus of the MEL attached to the implantable cardiac stimulation device, to the control circuitry within the MEL, during the initial charge balancing portion.

12. The implantable cardiac stimulation device of claim 9, wherein:

the controller is adapted to send the one or more commands, over the at least one of the two conductors of the multi-conductor bus of the MEL attached to the implantable cardiac stimulation device, to the control circuitry within the MEL, beginning a predetermined delay after a specified feature of a primary pace pulse portion of a cardiac pacing pulse produced by the pulse generator circuitry.

13. The implantable cardiac stimulation device of claim 9, wherein the one or more commands can be used to do one or more of:

query, change, refresh, or reset to a default, which one or more electrodes, if any, of the MEL is/are configured as an anode and which one or more electrodes of the MEL, if any, is/are configured as a cathode.

14. The implantable cardiac stimulation device of claim 9, wherein the pulse generator circuitry is adapted to produce a zero volt primary pace pulse portion and the controller is adapted to time the sending of the one or more commands relative to the zero volt primary pace pulse portion.

15. The implantable cardiac stimulation device of claim 9, wherein the controller is further adapted to send one or more further commands, over the at least one of the two conductors of the multi-conductor bus of the MEL attached to the implantable cardiac stimulation device, to the control circuitry within the MEL attached to the implantable cardiac stimulation device, instructing the MEL to enter or exit a low power mode, between instances when the switching circuitry is causing the sensing circuitry to be connected to the multi-conductor bus of the MEL and used to obtain the one or more signals indicative of cardiac electrical activity.

16. A method for use by an implantable cardiac stimulation device, the method for use when sending one or more commands to control circuitry within a multi-electrode lead (MEL) attached to the implantable cardiac stimulation device, wherein the MEL, which is attached to the implantable cardiac stimulation device, comprises a multi-conductor bus that includes two conductors, the method comprising:

sending one or more commands, over at least one of the two conductor of the multi-conductor bus of the MEL attached to the implantable cardiac stimulation device, to control circuitry within the MEL, during a predetermined portion of a cardiac pacing cycle such that the one or more commands are sent when cardiac tissue is refractory from a cardiac pacing pulse, wherein the cardiac pacing pulse includes a primary pace pulse portion and an initial charge balancing portion and a later charge balancing portion, wherein the charge balancing of the initial charge balancing portion is done at a faster rate than the charge balancing of the later charge balancing portion and wherein the sending step begins a predetermined delay after a specified feature of the primary pace pulse portion and during the initial charge balancing portion.

17. The method of claim 16, wherein the sending step is performed such that the one or more commands are sent between instances when sensing circuitry of the implantable cardiac stimulation device is connected to the multi-conductor bus of the MEL and is being used to obtain one or more signals indicative of cardiac electrical activity.

18. The method of claim 16, wherein the sending of the one or more commands interrupts charge balancing during the initial charge balancing portion.

19. The method of claim 16, wherein the one or more commands can be used to do one or more of:

query, change, refresh, or reset to a default, which one or more electrodes, if any, of the MEL is/are configured as an anode and which one or more electrodes of the MEL, if any, is/are configured as a cathode.

20. The method of claim 16, further comprising sending one or more further commands, over the at least one of the two conductors of the multi-conductor bus of the MEL attached to the implantable cardiac stimulation device, to the control circuitry within the MEL, instructing the MEL to enter or exit a low power mode, between instances when the sensing circuitry is connected to the multi-conductor bus of the MEL and is being used to obtain the one or more signals indicative of cardiac electrical activity.

21. An implantable cardiac stimulation device, comprising:

sensing circuitry adapted to selectively obtain, using electrodes selectively connected to the sensing circuitry, one or more signals indicative of cardiac electrical activity;

storage circuitry adapted to store data indicative of at least one of the one or more signals obtained using the sensing circuitry;

pulse generator circuitry adapted to selectively produce cardiac pacing pulses, wherein the said cardiac pacing pulses each includes a primary pace pulse portion and an initial charge balancing portion, wherein said initial charge balancing portion occurs after the primary pace pulse portion; and a controller adapted to send one or more electrode configuration commands, over at least one of two conductors of a multi-conductor bus of a multi-electrode lead (MEL) attached to the implantable cardiac stimulation device, to control circuitry within the MEL attached to the implantable cardiac stimulation device, during a predetermined portion of a cardiac pacing cycle such that the one or more electrode configuration commands are sent over the at least one of two conductors of the multi-conductor bus of the MEL when cardiac tissue is refractory from the cardiac pacing pulse, and wherein the controller is adapted to send the one or more electrode configuration commands over the at least one of the two conductors of the multi-conductor bus of the MEL beginning a predetermined delay after a specified feature of the primary pace pulse portion and during the initial charge balancing portion.

22. The implantable cardiac stimulation device of claim 21, wherein the controller is adapted to send the one or more commands over the at least one of the two conductors of the multi-conductor bus of the MEL between instances when sensing circuitry of the implantable cardiac stimulation device is connected to the multi-conductor bus of the MEL and is being used to obtain one or more signals indicative of cardiac electrical activity.

23. The implantable cardiac stimulation device of claim 21, wherein the controller is adapted to interrupt charge balancing in the initial charge balancing portion to send the one or more commands.

24. The implantable cardiac stimulation device of claim 21, wherein the one or more commands can be used to do one or more of:
 query, change, refresh, or reset to a default, which one or more electrodes, if any, of the MEL is/are configured as an anode and which one or more electrodes of the MEL, if any, is/are configured as a cathode.

25. The implantable cardiac stimulation device of claim 21, wherein the controller is further adapted to send one or more further commands, over the at least one of the two conductors of the multi-conductor bus of the MEL attached to the implantable cardiac stimulation device, to control circuitry within the MEL attached to the implantable cardiac stimulation device, instructing the MEL to enter or exit a low power mode, between instances when the switching circuitry is causing the sensing circuitry to be connected to the multi-conductor bus of the MEL and used to obtain the one or more signals indicative of cardiac electrical activity.

* * * * *